US00PP08124P

United States Patent [19]

van der Knapp

[11] Patent Number: Plant 8,124

[45] Date of Patent: Feb. 2, 1993

[54] CHRYSANTHEMUM PLANT — BAYFRANK CULTIVAR

[75] Inventor: Jacques C. M. van der Knapp, De Lier, Netherlands

[73] Assignee: Fides Beheer B.V., De Lier, Netherlands

[21] Appl. No.: 720,663

[22] Filed: Jun. 25, 1991

[51] Int. Cl.[5] ..... A01H 5/00

[52] U.S. Cl. ..... Plt./82.4

[58] Field of Search ..... Plt./74, 74.1, 82.4, Plt./76, 80

*Primary Examiner*—Howard J. Locker

*Attorney, Agent, or Firm*—Burns, Doane, Swecker & Mathis

[57] ABSTRACT

A new and distinct cultivar of Chrysanthemum plant named Bayfrank is provided. The new cultivar was the result of a controlled breeding program wherein the Bijoux cultivar (U.S. Plant Pat. No. 6,241) was pollinated by an unnamed seedling formed by the crossing of the Fleur cultivar (non-patented in the United States) by the Delta cultivar (U.S. Plant Pat. No. 5,815). More specifically, the new cultivar forms attractive relatively large anemone pink-purple flowers having a darker flower center (as illustrated). The inflorescence tends to assume a generally flat capitulum form when mature. The response period of the flowers is approximately eigh weeks. The new cultivar is particularly suited for use in the production of a cut anemone spray under greenhouse conditions.

1 Drawing Sheet

SUMMARY OF THE INVENTION

The present invention comprises a new and distinct cultivar of Chrysanthemum, botanically known as *Chrysanthemum morifolium*, Ramat., and hereinafter is referred to by the cultivar name Bayfrank.

The new cultivar is the product of a planned breeding program which had as its objective the creation of a new Chrysanthemum cultivar which exhibits attractive relatively large anemone flowers which are pink-purple in coloration, vigorous growth, a flower response period of approximately eight weeks, and the ability to produce flowers of commercially acceptable quality throughout the year in a cut mum production program. Such combination of traits is not believed to have been present in the previously available Chrysanthemum cultivars. This objective was satisfactorily fulfilled in the cultivar of the present invention.

The breeding program which resulted in the production of the new cultivar of the present invention was carried out in a controlled environment during 1984 at De Lier, The Netherlands. The female parent (i.e., the seed parent) was the Bijoux cultivar (U.S. Plant Pat. No. 6,241) and the male parent (i.e., the pollen parent) was an unnamed seedling formed by the crossing the Fleur cultivar (non-patented in the United States) by the Delta cultivar (U.S. Plant Pat. No. 5,815). The parentage of the new cultivar can be summarized as follows:

Bijoux × (Fleur × Delta).

The seeds resulting from the above pollination were sown and plantlets were obtained which were physically and biologically different from each other. Selective study during January, 1986 resulted in the identification of a single plant of the new variety.

It was found that the new cultivar of the present invention:

(a) exhibits attractive relatively large anemone pink-purple flowers having a darker center, (b) bears flowers in a generally flat capitulum configuration when mature, (c) exhibits a flower response period of approximately eight weeks, (d) forms attractive dark green foliage, and (e) has the ability to produce flowers of commercially acceptable quality throughout the year in a cut mum production program.

Asexual reproduction of the new cultivar by cuttings initially taken during 1985, as performed at De Lier, The Netherlands, in a controlled environment has demonstrated that the characteristics of the new cultivar as herein disclosed are firmly fixed and are retained through successive generations of asexual propagation.

Bayfrank has not been observed under all possible environmental conditions to date. Accordingly, it is possible that the phenotype may vary somewhat with variations in the environment, such as temperature, light, day length, contact with pesticides and/or subjection to growth retardant treatments.

When the new cultivar of the present invention is compared to the Warrant cultivar (non-patented in the United States), the Bayfrank cultivar is found to exhibit a smaller flower size, (e.g., an overall flower diameter of approximately 70 to 90 mm. vs. approximately 100 mm.), less vegetative growth (e.g., assumes a height of approximately 110 cm. vs. approximately 125 cm.), exhibits less tolerance to white rust, and exhibits less tolerance to low temperature. The anemone type flower, the pink-purple ray floret coloration, and the response time of the Bayfrank cultivar are substantially identical to the corresponding characteristics of the Warrant cultivar.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at De Lier, The Netherlands.

DETAILED DESCRIPTION

The chart used in the identification of colors described hereafter is the R.H.S. Colour Chart of The Royal Horticultural Society, London, England. The color values were determined at 11:00 a.m. to 12:00 noon under natural daylight conditions at De Lier, The Netherlands, on Mar. 31, 1991. The plants described were grown under standard greenhouse conditions which approximate those commonly utilized for the production of cut mums.

Classification:

*Botanical.*—*Chrysanthemum morifolium* Ramat., cv. Bayfrank.

*Commercial.*—Cut anemone spray.

INFLORESCENCE

A. Capitulum:

*Form.*—Generally flat when mature.

*Type.*—Anemone.

*Diameter across face.*—Approximately 70 to 90 mm. on average.

*Diameter of flower center.*—Approximately 25 mm. on average.

B. Corolla of ray and disc florets:

*Color (general tonality from a distance of three meters).*—Pink-purple with darker center.

*Color ray florets. (top surface).*—Generally pink-purple, ranges from Red-Purple Group 65D to Purple Group 76D.

*Color disc florets.*—Generally a darker pink-purple than the ray florets, ranges from Red-Purple Group 65B to Purple Group 76A.

C. Reproductive organs:

*Androecium.*—Present in disc florets.

*Gynoecium.*—Present in disc florets.

PLANT

A. General appearance:

*Height.*—Approximately 110 cm. on average.

B. Foliage:

*Color (upper surface).*—Yellow-Green Group 147A.

*Color (under surface).*—Yellow-Green Group 147B.

I claim:

1. A new and distinct cultivar of Chrysanthemum plant named Bayfrank, substantially as herein shown and described, which:

(a) exhibits attractive relatively large anemone pink-purple flowers having a darker center, (b) bears flowers in a generally flat capitulum configuration when mature, (c) exhibits a flower response period of approximately eight weeks, (d) forms attractive dark green foliage, and (e) has the ability to produce flowers of commercially acceptable quality throughout the year in a cut mum production program.

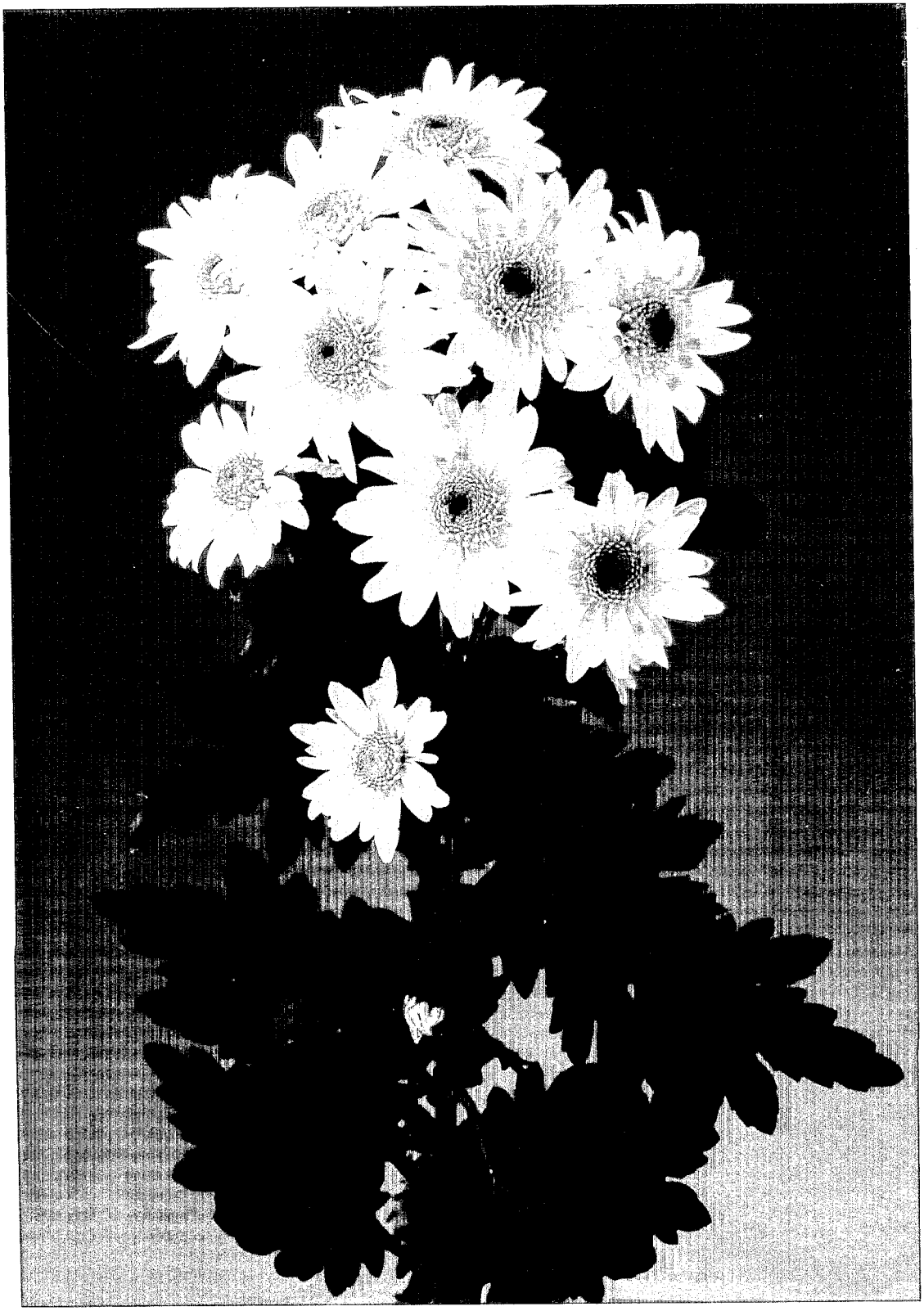

* * * * *